Jan. 16, 1973 D. B. LOWRY Plant Pat. 3,291
PEAR TREE
Filed July 8, 1971
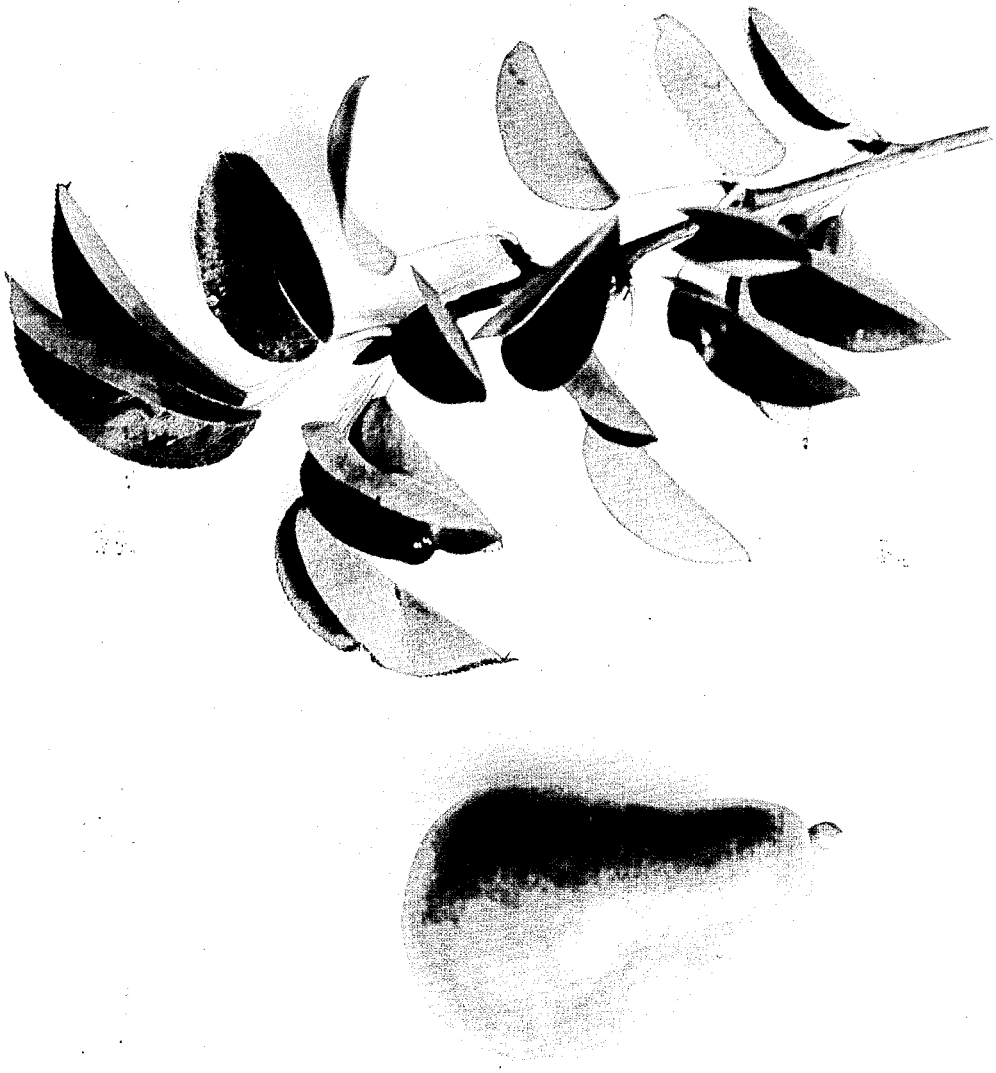
INVENTOR
David B. Lowry
BY
Webster & Webster
ATTORNEYS United States Patent Office Plant Pat. 3,291
Patented Jan. 16, 1973

3,291
PEAR TREE
David B. Lowry, 5500 Colver Road,
Talent, Oreg. 97540
Filed July 8, 1971, Ser. No. 160,872
Int. Cl. A01h 5/03
U.S. Cl. Plt.—36 1 Claim

ABSTRACT OF THE DISCLOSURE

A fast-growing, medium-size, medium-vigorous, upright, tall, open, vase-formed, hardy pear tree which is a regular and productive bearer of medium-size fruit, of good market quality, having red skin and white flesh; the red skin being thick, smooth, waxen, and glossy, and the flesh being firm, tender, juicy, subacid, and distinctly white.

ORIGIN OF THE VARIETY

The present variety of pear tree was originated by me on a ranch, of which I am an owner, as a cross between the Forelle (unpatented) and the Max-Red Bartlett (United States Plant Patent No. 741); such ranch being located in Jackson County, near Talent, Oreg. When the hybrid seedlings resulting from such cross grew to maturity and bore fruit, one such seedling, and which is the present variety, evidenced novel and distinct characteristics. Upon recognition by me of such characteristics, I selected the variety for asexual reproduction preparatory to ultimate commercial growing thereof.

ASEXUAL REPRODUCTION OF THE VARIETY

The present variety of pear tree was asexually reproduced by me as grafts on mature Bosc (unpatented) pear trees in an orchard on the aforesaid ranch. In maturity, such asexual reproductions ran true to the original tree in all respects.

SUMMARY OF THE VARIETY

The present variety of pear tree is fast growing, medium size, medium vigorous, upright, tall, open, vase-formed, hardy, and—with the advantages of a hybrid as compared to a mutation—a regular and productive bearer of medium-size fruit, of good market quality, having red skin and white flesh.

The red skin of the fruit, of the present variety, is thick, smooth, waxen, and glossy as compared, for example, to the yellow, thin, smooth, and slightly waxy skin of the Bartlett (unpatented); and as compared, for further example, to the green, slightly rough, medium thick, dull skin of the Anjou (unpatented).

The flesh of the fruit, of the present variety, is firm, tender, juicy, subacid, and distinctly white as compared, for example, to the sweet (without acid), slightly yellowish white flesh of both the Bartlett and the Anjou.

In comparative form, the fruit, of the present variety, is as wide as but shorter and less pyriform than the Bartlett; and while resembling the Anjou in size and shape, is slightly longer and slightly more pyriform.

In general, the fruit of the present variety has, desirably, the red color of the Forelle, with a market quality approaching that of the Bartlett; the latter, of course, being—to date—the most widely commercially grown variety of pear tree.

BRIEF DESCRIPTION OF THE DRAWING

The drawing is an illustration, by photographic reproduction in color, of a twig with leaves, and a fruit, detached.

DESCRIPTION OF THE VARIETY

The botanical details of this new and distinct variety of pear tree—with color definitions (except those in common color terms) referenced to Maerz and Paul Dictionary of Color—are as follows:

Tree:
- *Size.*—Medium.
- *Vigor.*—Medium.
- *Growth.*—Upright; tall; rapid; open.
- *Form.*—Vase-formed.
- *Hardiness.*—Hardy.
- *Production.*—Productive.
- *Bearing.*—Regular bearer.

Trunk:
- *Size.*—Medium.
- *Texture.*—Medium.

Branches:
- *Size.*—Medium.
- *Texture.*—Smooth.
- *Color.*—Brown-gray.
- *Lenticels.*—Number—Few. Size—Medium.

Leaves:
- *Size.*—Small. Length—Short—1¾"–2¾"—average 2¼". Width — Medium — 1⅜"–1 3/16" — average 1½".
- *Form.*—Ovate; abruptly pointed.
- *Thickness.*—Medium.
- *Texture.*—Glabrous.
- *Margin.*—Glandular, finely serrate.
- *Petiole.*—Length—medium 1"–1½"—average 1¼". Thickness—Medium. Texture—Glabrous.
- *Color.*—Top side—Medium green (23–L–8). Under side—Lighter green (22–I–4).

Buds:
- *Size.*—Small.
- *Texture.*—Bronze hairs on margins of bud scales, and on other exposed surfaces.

Flowers:
- *Blooming period.*—Late—April 28–May 3, 1971—later than Bartlett; same as Bosc.
- *Size.*—Medium.
- *Color.*—Pink in bud, white with flecks of pink in full bloom.
- *Fertility.*—Self-sterile.

Fruit:
- *Ripening period.*—First picking—August 15. Last picking September 20th.
- *Retention.*—Hangs well.
- *Size.*—Medium; length (well grown specimen)—3¾"; width (well grown specimen)—2½"–2¾"; variable.
- *Form.*—Oblong-obviate; sides unequal.
- *Stem.*—Short—½"; medium thickness.
- *Cavity.*—Shallow; narrow; smooth; symmetrical.
- *Calyx.*—Closed; small. Lobes.—Separated at base; short; medium width; obtuse.
- *Basin.*—Medium depth; medium width; obtuse; smooth.

Skin:
- *Thickness.*—Thick.
- *Texture.*—Smooth; waxen; glossy.
- *Color.*—Red (7–J–6) over yellow (11–L–6) ground color, with numerous, large gray areolar dots.

Flesh:
- *Color.*—White (9–B–1).
- *Texture.*—Firm; tender; juicy.
- *Flavor.*—Subacid.
- *Eating quality.*—Good.
- *Core.*—Medium size; closed; axile.
- *Core lines.*—Meeting.
- *Calyx tube.*—Length—medium.

*Width.*—Medium.
*Form.*—Funnel-shaped.
*Seed.*—Medium size; plump; acute.
Use: Dessert; market.
Keeping quality: Good.
Shipping quality: Good.

THE PRESENT VARIETY AS COMPARED TO THE BARTLETT

The leaves are slightly shorter and slightly narrower than Bartlett. The shape of the leaves is similar to Bartlett; they being flat, ovate, abruptly pointed and medium green. However, the leaves are glabrous while Bartlett is tomentose along the midrib on both the upper and lower sides. Both varieties have finely serrate leaf margins which are glandular.

The buds are medium size and have bronze hair on scale surfaces and margines, while Anjou buds are small and have bronze hair on bud scale margins only.

The fruit is as wide as but shorter than Bartlett and less pyriform. The length/width raio is 1.23 compared to 1.45 for Bartlett.

The stem is only ½ inch long and rather stout, while Bartlett stems are ⅘ inch long, slender, and with an enlargement on the abscission end.

The cavity is minor in both varieties with no marked differences.

The calyx of both varieties is closed.

The basin is distinctly deeper than on Bartlett, with the closed calyx lobes below the level of the shoulders.

The skin is red, thick, smooth, waxen, and glossy, while the skin of a ripe Bartlett is yellow, thin, smooth, and slightly waxy.

The dots are distinctly areolar reflecting the Forelle parentage, while the Bartlett dots have no areolar condition.

The flesh is distinctly white and has a subacid flavor, while Bartlett has a slightly yellowish white and is sweet with no indication of acidity.

The fruit quality is good, whereas the quality of Bartlett is best.

THE PRESENT VARIETY AS COMPARED TO THE ANJOU

The leaves are ½ inch shorter and very slightly wider than Anjou. The leaves are flat, ovate, and abruptly pointed, whereas Anjou leaves are longer and recurved. Anjou leaves also tend to have a yellowish cast compared to the green of the present leaves. The leaves are glabrous, whereas the Anjou is lightly tomentose below. The leaf margin is glandular and finely serrate, while the margin on Aanjou is crenate and glands are few or missing.

The buds are medium size and have bronze hair on bud scale surfaces and margins, while Anjou buds are small and have bronze hair on scale margins only.

The fruit resembles Anjou in size and shape but is slightly longer and a little more pyriform. The length/width ratio is 1.23, while the Anjou is only 1.15.

The stem on both varieties is ½ inch long.

The cavity is very minor and not typically marked, while on Anjou there is a distinct cavity which is well russeted and the shouders rounded.

The calyx is closed, while the Anjou calyx is open.

The basin is distinctly deeper than on Anjou, with the closed calyx lobes below the level of the shoulders. Anjou has a very small basin with the open calyx lobes level with or exceeding the shoulders.

The skin is red, thick, smooth, waxen, and glossy, while the skin of Anjou is green, slightly rough, medium thick, and dull.

The dots are distinctly areolar reflecting the Forelle parentage, while the Anjou dots have no areolar condition.

The flesh is distinctly white and has a subacid flavor, while Anjou has a slightly yellowish white and is sweet with no indication of acidity.

The quality of both varieties is good.

VARIANCE IN BOTANICAL DETAILS

The pear tree and its fruit herein described may vary in slight detail due to climatic and soil conditions under which the variety may be grown; the present description being of the variety as grown in the Jackson County area of Oregon.

I claim:

1. A new and distinct variety of pear tree, substantially as illustrated and described, which is fast growing, medium size, medium vigorous, upright, tall, open, vase-formed, hardy, and a regular and productive bearer of medium size fruit, of good market quality, having red skin and white flesh; the red skin being thick, smooth, waxen, and glossy, and the flesh being firm, tender, juicy, subacid and distinctly white.

No references cited.

ROBERT E. BAGWILL, Primary Examiner